United States Patent [19]

Ringot et al.

[11] Patent Number: 5,328,662

[45] Date of Patent: Jul. 12, 1994

[54] INSTALLATION FOR CARRYING OUT SEVERAL SUCCESSIVE CHEMICAL REACTIONS IN THE SAME CONTAINER

[75] Inventors: Gilbert Ringot, Querqueville; Pierre Digard, Touvlaville, both of France

[73] Assignee: Cogema-Compagne Generale Des Matieres Nucleaires, France

[21] Appl. No.: 942,295

[22] Filed: Sep. 9, 1992

[30] Foreign Application Priority Data

Sep. 10, 1991 [FR] France ............................ 91 11144

[51] Int. Cl.⁵ ............................................ G01N 35/00
[52] U.S. Cl. .......................................... 422/63; 422/64; 422/67; 422/75; 422/159; 422/225; 423/124; 423/249
[58] Field of Search ................ 422/63, 64, 67, 159, 422/225, 75; 423/12, 20, 11, 7, 16, 6, 124, 155, 249, 253; 210/721; 204/157.52

[56] References Cited

U.S. PATENT DOCUMENTS

| | | | |
|---|---|---|---|
| 3,501,064 | 3/1970 | Gaumer | 222/358 |
| 3,578,408 | 5/1971 | Sirois et al. | 422/75 X |
| 3,663,178 | 5/1972 | Miller et al. | 422/159 X |
| 3,682,598 | 4/1972 | Kaartinen | 422/159 |
| 3,723,180 | 3/1973 | Brown | 423/6 X |
| 3,866,476 | 2/1975 | Thomas | 73/423 |
| 4,145,396 | 3/1979 | Grantham | 423/22 |
| 4,152,395 | 5/1979 | Börner et al. | 423/16 |
| 4,180,476 | 12/1979 | Anav et al. | 423/249 X |
| 4,215,091 | 7/1980 | Petersen et al. | 422/75 |
| 4,224,258 | 9/1980 | Langen et al. | 422/159 X |
| 4,239,970 | 12/1980 | Eckhardt et al. | 422/159 X |
| 4,255,393 | 3/1981 | Chiang | 423/15 |
| 4,271,127 | 6/1981 | Borner et al. | 422/159 |
| 4,297,105 | 10/1981 | Dube | 422/75 X |
| 4,344,872 | 8/1982 | Thiele | 422/159 X |
| 4,347,141 | 8/1982 | Rothberg | 210/721 |
| 4,353,803 | 10/1982 | Dover, Jr. | 210/728 |
| 4,377,508 | 3/1983 | Rothberg | 423/11 X |
| 4,427,639 | 1/1984 | Himsley | 423/7 |
| 4,439,402 | 3/1984 | Tarutani et al. | 422/159 |
| 4,457,893 | 7/1984 | Takekawa | 422/64 |
| 4,483,823 | 11/1984 | Umetsu et al. | 422/63 |
| 4,541,902 | 9/1985 | Kinoshita et al. | 422/75 X |
| 4,554,255 | 11/1985 | Ishii et al. | 436/102 |
| 4,576,802 | 3/1986 | Floreancig | 423/20 |
| 4,636,367 | 1/1987 | Huck et al. | 423/12 |
| 4,637,867 | 1/1987 | Herbst | 204/157.52 |
| 4,732,742 | 3/1988 | Puig | 423/119 |
| 4,748,008 | 5/1988 | Takeda et al. | 423/6 |
| 4,865,992 | 9/1989 | Hach et al. | 436/51 |
| 4,950,610 | 8/1990 | Tittle | 436/163 |
| 4,999,305 | 3/1991 | Wolcott et al. | 436/52 |

FOREIGN PATENT DOCUMENTS

55-082054 9/1980 Japan.
58-120166 10/1983 Japan.

Primary Examiner—James C. Housel
Assistant Examiner—Harold Y. Pyon
Attorney, Agent, or Firm—Pearne, Gordon, McCoy & Granger

[57] ABSTRACT

The disclosure describes an apparatus for performing at least two successive chemical reactions in the same container. In order to successively carry out several chemical reactions in the same container (10), e.g. dosing uranium in the presence of plutonium and fission products, the container is placed in a working station above which issue tubes (16, 20) for supplying the products necessary for the reactions. When a product has to be introduced, a computer controls the descent of the corresponding tube. When the product may react inopportunely if it drops into the container (10) outside the time intended for this purpose, the lower end of the product supply tube (16) is automatically laterally displaced with respect to the container, when the tube is in the top position, e.g. by the cooperation of a pawl (102) with a slot (100) forming a cam.

12 Claims, 4 Drawing Sheets

INSTALLATION FOR CARRYING OUT SEVERAL SUCCESSIVE CHEMICAL REACTIONS IN THE SAME CONTAINER

BACKGROUND OF THE INVENTION a. Field of the Invention

The present invention relates to an installation for carrying out several successive chemical reactions within the same container.

Such an installation can be used in numerous cases, particularly when it is wished to automate a succession of chemical reactions, so as to be able to e.g. dose a reactant. Thus, the installation according to the invention can be used for the automated performance of the dosing of uranium in the presence of plutonium and fission products, in the aqueous or organic phase, using the Davies and Gray method, as specified in the method of International Standard ISO 7097-1983 (E) (hereinafter referred to as "the Davies and Gray method").

b. Description of the Prior Art

When several chemical reactions have to be performed successively in the same container, consideration can be given to the displacement of said container between successive stations at the level of which are introduced different products. However, this can lead to the installation having large overall dimensions when a considerable number of chemical reactions have to be performed. Moreover, the satisfactory performance of the reactions may be incompatible with a displacement of the container between the successive introduction of two reactants into it. Moreover, this solution causes the problem of the stirring of the mixed reactants and in particular the checking of the satisfactory performance of the different reactions.

Another solution consists of making all the reactants arrive at the same point in order to carry out together the chemical reactions without moving the container. This leads to the solution of the problems of the overall dimensions, stirring and checking the satisfactory performance of the reactions.

However, the latter solution leads to the placing of the end of each of the distribution tubes for the different reactants and reagents above the container. This can have the consequence of a drop of reactant and in particular a reagent falling inopportunely into the container during the performance of the different reactions. This is clearly unacceptable, because the results can be completely falsified, particularly when a reactant is being dosed. Moreover, no matter what procedure is used, the problem caused by the rinsing and emptying of the container when all the operations are finished is also difficult to solve.

SUMMARY OF THE INVENTION

The invention specifically relates to an installation in which several chemical reactions are performed successively within the same container without moving the latter and without a drop of reactant and particularly reagent falling accidentally into the container inopportunely during the performance of the reactions.

According to the invention, this result is obtained by means of an installation for performing several successive chemical reactions within the same container, characterized in that it incorporates at least two reactant arrival tubes, control means able to separately displace a lower end of each of the tubes between an upper, inactive position and a lower, reactant injection position, as well as means for laterally displacing the lower end of at least one first tube, under the effect of an actuation of said control means, so that said lower end is placed in the container in the bottom position and is laterally displaced with respect to the container in the top position.

In a thus designed installation, the tube or tubes laterally displaced so as not to be placed above the container when they are in the top position are chosen as a function of the reactants which they carry, so that all reagents which may disturb the performance of the chemical reactions can in no case accidentally drop inopportunely into the container during the performance of these reactions.

In a preferred embodiment of the invention, the first tube has a straight, vertically axed part, able to slide and rotate in a support, the lower end of said first tube being displaced relative to said vertical axis, and means for displacing the said lower end incorporating means for pivoting the first tube around said vertical axis. Preferably, the means for pivoting the first tube then have a finger or pawl integral with the straight part of the latter and which is received in an inwardly curved slot formed in the support.

Moreover, the reactants arrival tubes advantageously incorporate a tube for supplying liquid for rinsing and emptying the container, having at its lower end a h-shaped ramp, whereof a branched off, short branch enters the container and whereof a rectilinear, long branch, outside the container, has a narrowing below the connection of the short branch.

The installation preferably also comprises a vertical electrode for checking the chemical reactions, arranged in bundle-like manner with the tubes and on which also act the control means.

Moreover, an electromagnetic stirrer is advantageously placed beneath the container, a magnetic bar preferably having a triangular cross-section being placed in a circular recess formed in the container bottom.

In order that the same succession of chemical reactions can be successively performed in several containers, the installation can also comprise moving means making it possible to in turn supply several containers to a working station, above which are located the lower ends of the tubes. Said moving means can in particular comprise a horizontal table having container reception cavities, which are regularly distributed about a vertical axis, together with driving means making it possible to sequentially turn the table around its axis when the successive chemical reactions are terminated for a given container.

The successive chemical reactions are automatically performed as a result of the intervention of a control station, which controls the control means and the means for distributing the reactants within the tubes.

When the reactant or reactants used make it necessary, the container is placed in a tight confinement enclosure, whereof an upper wall is provided with a plate tightly traversed by the product supply tubes, said plate supporting a container-holding beam within the enclosure and control means outside the enclosure.

BRIEF DESCRIPTION OF THE DRAWINGS

The invention is described in greater detail hereinafter relative to non-limitative embodiments and with reference to the attached drawings, wherein show.

DESCRIPTION OF THE PREFERRED EMBODIMENT

In the embodiment illustrated in FIGS. 1 to 5, the installation according to the invention is applied to the dosing of uranium, in the presence of plutonium and fission products, in the aqueous or organic phase and using the Davies and Gray method. As has already been stated, this application must not be considered as limiting the scope of the invention, which can be used whenever several chemical reactions have to be successively performed within the same container, particularly but not exclusively in order to carry out a dosing therein.

Figure 1:
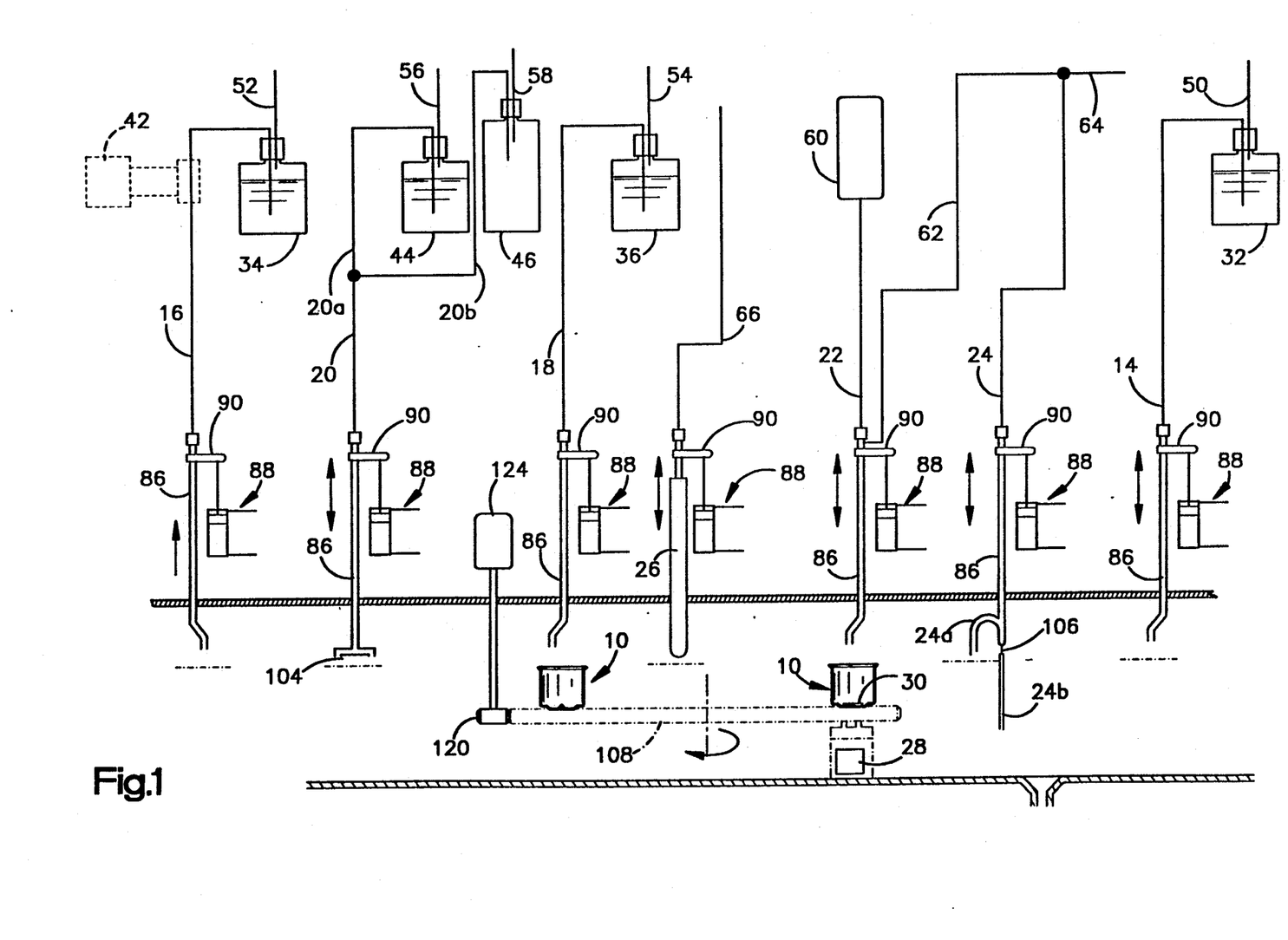
FIG. 1 A diagram very diagrammatically illustrating an installation according to the invention applied to the automatic dosing of uranium according to the Davies and Gray method.

In the application of the invention to the dosing of uranium, the sampled solutions to be dosed are placed in containers such as cups or beakers 10, which are located within a tight, shielded confinement enclosure 12. To enable the dosing to be carried out, each of the cups 10 must in turn be brought in front of a working station above which issue several product supply tubes 14, 16, 18, 22, a cup emptying and rinsing liquid supply tube 24 and a diluting mixture supply tube 20. This working station is also equipped with a measuring electrode 26 making it possible to check the evolution of the reactions occurring in the cup and an electromagnetic stirrer 28. In the embodiment shown, these different elements make it possible to carry out at the working station the dosing of uranium in accordance with the Davies and Gray method by carrying out the successive operations which will now be briefly described.

Firstly the operator introduces manually into the cup 10, which is not yet located at the working station, the sample to be dosed and which contains 50 to 200 mg of uranium, as well as three drops of 2% potassium dichromate and 5 cm$^3$ of 1N nitric acid.

The cup is then placed in the working station, where the following operations are performed in turn:

introduction of 5 cm$^3$ of sulphamic acid and 45 cm$^3$ of reducing reactive mixture (phosphoric iron $H_3PO_4$/$FeSO_4$), whilst stirring at low speed for 1 min.;

introduction of 10 cm$^3$ of oxidizing reagent (molybdate) whilst stirring at a higher speed (a brown colouring appearing and then the solution must become light green again in the following 40 seconds);

continuing the stirring for about 2½ minutes and then allowing to stand for 30 seconds;

introduction of a dilution mixture (5 cm$^3$ of vanadyl sulphate and 100 cm$^3$ of distilled water) accompanied by vigorous stirring;

introducing the titrating solution (potassium dichromate) approximately 60 seconds later.

It is important to note that all these operations must be carried out in order to ensure that the arrival at the inflexion point corresponding to the end of dosing occurs within the 4 minutes following the dilution of the reaction medium.

The performance of this process in the installation according to the invention therefore makes it necessary to introduce into the cup 10 located at the working station sulphamic acid by the first tube 14, the reducing reactive mixture by the second tube 16, the oxidizing reagent by the third tube 18, the dilution mixture by the fourth tube 20 and the titrating solution by the fifth tube 22 in the form of a catheter. With said reagent, diluent and titrating solution supply tubes 14, 16, 18, 20 and 22 are associated the tube 24 for supplying the rinsing and emptying liquid for the container and the electrode 26. The stirring of the solution contained in the cup 10 located at the working station is carried out by an electromagnetic stirrer 28 associated with a magnetic bar 30 placed in the cup bottom.

Each of the tubes 14, 16 and 18 is immersed by its end opposite to that located inside the enclosure 12 in a distribution drum 32, 34, 36 respectively, located outside the enclosure 12 and respectively containing sulphamic acid, the reducing reactive mixture and the oxidizing reactive mixture. A normally closed electrovalve, as shown at 38 in FIG. 2 for the tube 14, is placed at the outlet of each of the drums 32, 34, 36 in each of the tubes 14, 16, 18. These electrovalves are controlled by a central control computer 40 programmed so as to perform the desired dosing process.

As illustrated in FIG. 1, the reducing reactive mixture contained in the drum 34 is preheated between said drum and the corresponding electrovalve by a preheating system 42 to a temperature of approximately 50 C., so that the reaction medium is at a temperature of approximately 35 C. during the destruction of the excess reducing agent. The preheating system 42 can in particular be constituted by a thermostatic bath in which the phosphoric iron is preheated by circulation in a double glass envelope container.

The tube 20 by which is introduced the dilution solution has, outside the enclosure 12, two branches 20a, 20b, whose ends are respectively immersed in a drum 44 containing vanadyl sulphate and in a drum 46 containing distilled water. Each of the branches 20a, 20b of the tube 20 is also equipped with a normally closed electrovalve 48, 49 (FIG. 2), whose opening is controlled in programmed manner by the central control computer 40.

In order that the opening of any one of the electrovalves, such as the electrovalves 38, 48, 49 placed in the different distribution tubes 14, 16, 18 and in the branches 20a and 20b of the tube 20 leads to an injection of the reagent or the corresponding reactant, the different drums 32, 34, 36, 44 and 46 containing said reagents and reactants are placed under pressure by a not shown, compressed air circuit. Only the tubes 50, 52, 54, 56 and 58 of said compressed air circuit and which respectively issue at the top of the drums 32, 34, 36, 44 and 46 have been shown in FIG. 1.

The catheter-forming tube 22 by which is supplied the titrating solution is connected outside the enclosure 12 to an electroburette 60 controlled by the central control computer 40. Said electroburette 60 more particularly makes it possible to check the titrating solution introduction speed by acting on a not shown tap equipping the burette. Pulses representing the titrating solution volume which have flowed out are transmitted in return to the computer.

As is also diagrammatically illustrated in FIG. 1, a tube 62 for supplying a rinsing liquid such as water is branched to the catheter-forming tube 22, so as to permit the rinsing of that part of the tube which issues into the enclosure 12, when the titrating solution has been introduced by means of the electroburette 60. The rinsing liquid introduction by the tube 62 is checked by a not shown electrovalve controlled by the central control computer 40. At its opposite end, the tube 62 is connected to a demineralized water supply circuit 64.

The tube 24 for supplying the rinsing and draining liquid for the cup 10 is also connected, outside the enclosure 12, to the demineralized water supply circuit 64. Downstream of its connection to the circuit 64, the tube 24 also has a normally closed electrovalve 65 (FIG. 2) controlled by the central control computer 40.

The measuring electrode 26 is directly connected to the central control computer 40 by an electric cable 66. It makes it possible to permanently measure the evolution of the potential of the solution contained in the cup 10 located at the working station, by comparison with a not shown reference electrode positioned outside the enclosure 12.

Figure 2:
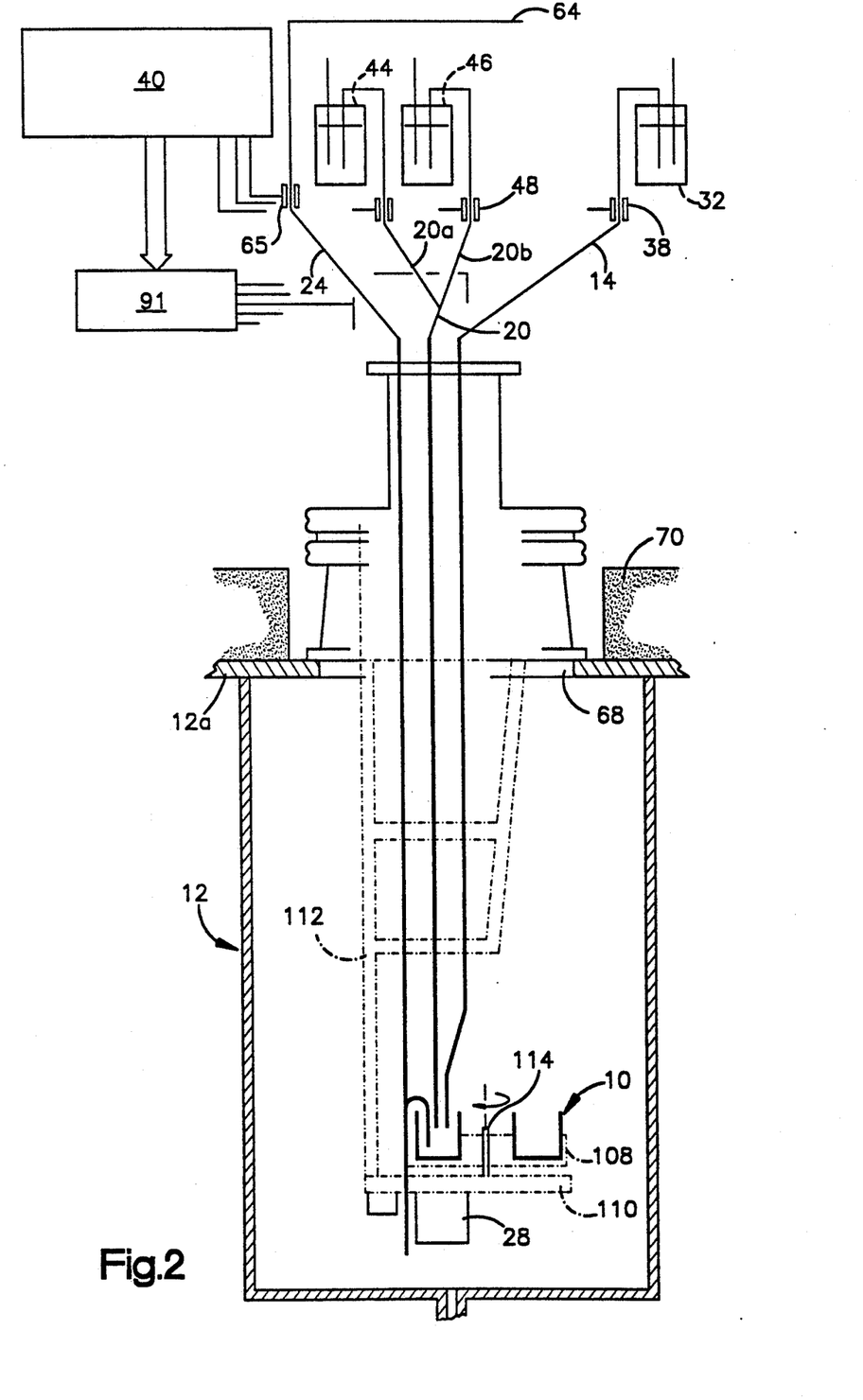
FIG. 2 A part vertical sectional view very diagrammatically illustrating the installation according to the invention.
Figure 3:
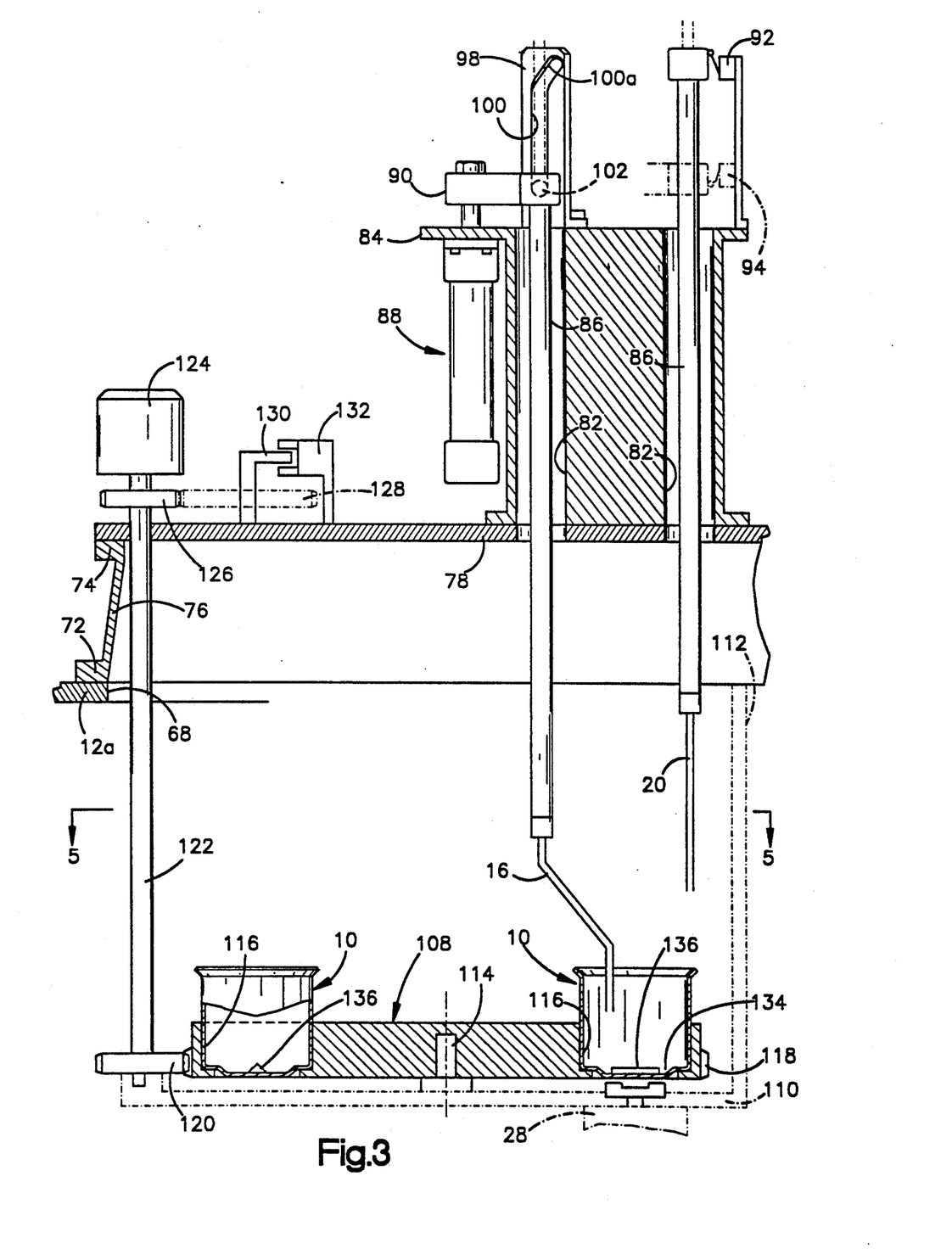
FIG. 3 A vertical sectional, side view in greater detail of the mechanical part of the installation according to the invention.
Figure 4:
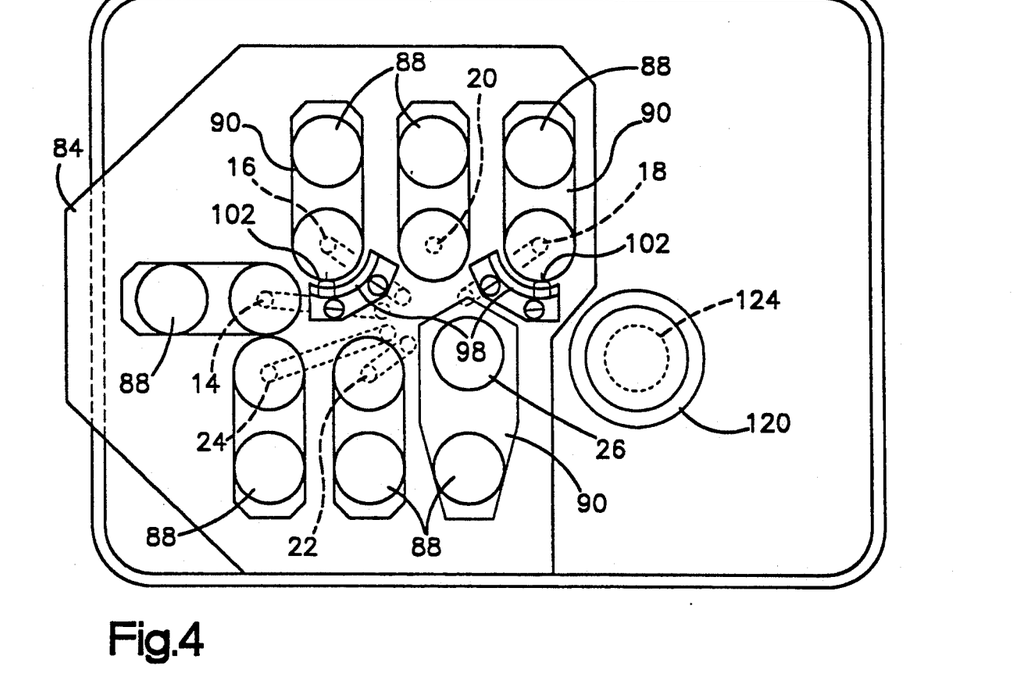
FIG. 4 A plan view of the mechanical part illustrated in FIG. 3.

In practice and as is more particularly illustrated by FIGS. 2 to 4, the mechanical part of the dosing installation diagrammatically illustrated in FIG. 1 is installed on the upper wall 12a of the enclosure 12. For this purpose a rectangular opening 68 is made in the upper wall 12a, as well as in the shield 70 (FIG. 2), which overhangs said wall. A lower flange 72 (FIG. 3) having the shape of the opening 68 is tightly fixed to the upper wall 12a by not shown means, such as screws. An upper flange 74, located above the upper face of the shield 70, is joined to the lower flange 72 by a passage 76.

A horizontal support plate 78 rests on the upper flange 74 and is joined tightly thereto by not shown fixing means, such as screws. To said plate 78 is also tightly fixed, e.g. by not shown screws, a solid body 80 traversed by seven vertical bores 82, whereof only two are visible in FIG. 3. Screws or any other not shown fixing means make it possible to fix a horizontal plate 84 to the upper face of the body 80.

A sliding ramp 86 is received in each of the bores 82 formed in the body 80 and also traverses the plates 78 and 84. Each of these ramps 86 supports along its axis a straight, vertical part of one of the tubes 14, 16, 18, 20, 22 or 24 or the electrode 26. Each ramp 86 can be displaced in the corresponding bore 82 between a top position and a bottom position by control means constituted by a double acting hydraulic jack 88, whose body is fixed beneath the plate 84 and whose vertical control rod projects above the plate 84 and is connected by its upper end to the upper end of the corresponding ramp 86 by a strap bolt 90, as illustrated in FIG. 3. As is shown under the general reference 91 in FIG. 2, each of the two chambers of each hydraulic jack 88 is connected by a pipe to a hydropneumatic interface by means of a flow reducer and each hydropneumatic interface communicates with a compressed air circuit by means of an electrovalve controlled by the central control computer 40.

A position change of the electrovalve associated with any random one of the jacks 88, under the action of the central control computer 40 makes it possible, as a function of the particular case, either to lower the corresponding ramp 86 or in order to inject a reactant or reagent into the cup 10 located at the working station, or conversely to raise said ramp after the introduction into the cup of the corresponding reactant or reagent.

As is very diagrammatically shown for one of the ramps 86 in FIG. 3, the extreme top and bottom positions of each of the ramps 86 are referenced by two optoelectronic sensors 92, 94 mounted on a support 96 fixed to the upper face of the plate 84. Each of these sensors such as 92 and 94 is connected to the central control computer 40.

When a signal indicating the presence of the upper end of the corresponding ramp 86 is supplied by one of the sensors 92 and 94 to the central control computer 40, the electrovalve corresponding to the jack 88 associated with said ramp is brought into a neutral position, in which the jack is kept in the position which it occupies.

For the satisfactory performance of the dosing process performed with the aid of the installation shown in the drawings, it is essential that certain reagents cannot be inopportunely introduced into the cup 10 at the working station. In particular, it is imperative that drops of the reducing reactive mixture such as phosphoric iron supplied by the tube 16 or drops of the oxidizing reagent such as the molybdate introduced by the tube 18 cannot drop into the cup 10 outside the periods during which said reagent must be introduced into it.

To this end, the installation according to the invention has means making it possible to automatically displace the lower end of the tubes 16 and 18, so that they are not positioned above the cup 10 at the working station, when the ramps 86 supporting each of the said tubes is in the top position.

In practice, these means make it possible to automatically pivot the corresponding ramps 86 about their own axes when they are approaching their top position. Thus, for overall dimensional reasons which can be more clearly gathered from FIG. 5, the vertical axes of the lower ends of the product supply tubes, with the exception of the axis of the dilution product supply tube 20, are laterally displaced with respect to the axes of the ramps 86 supporting the straight parts of these tubes. The pivoting of the ramps 86 supporting the tubes 16 and 18, when said ramps come into the top position, therefore has the effect of bringing the lower end of each of the tubes into a laterally displaced position with respect to the outer envelope of the cup 10 positioned at the working station.

In order to pivot the two ramps 86 carrying the tubes 16 and 18, the rotary ramps 86 are mounted on strap bolts 90 and to the upper face of the plate 84 are fixed two guidance members 98, each having, in horizontal section, the shape of a circular arc centered on the axis of the corresponding ramp 86. In each of the parts 98 is made an inwardly curved oblong slot 100 forming a cam, in which is received a pawl 102, which projects radially towards the outside from the upper end of the corresponding ramp 86. Each of the slots 100 is oriented parallel to the axis of the corresponding ramp 86 over most of its height, with the exception of its upper part 100a, which is helically inclined in order to bring about the desired pivoting of the ramp 86 carrying the tube 16 or 18, when said ramp approaches its top position. Advantageously, the pawl 102 is provided with a not shown roller in order to reduce friction.

As is diagrammatically illustrated in FIG. 1, the bottom part of each of the tubes 14, 16, 18 and 22 is essentially shaped like a horizontally positioned Z, so that the lower end is laterally displaced with respect to the straight part received in the corresponding ramp 86.

Moreover, the lower end of the tube 20, which is rectilinear, is connected to a T-shaped ramp 104 (FIG. 1) facilitating the dilution of the mixture introduced by the said tube.

With regards to the lower part of the container rinsing and draining liquid supply tube 24, it is shaped like a h, whose short branch 24a has a length shorter than that of the long, rectilinear branch 24b. Moreover, the rectilinear branch 24b has a restriction 106 immediately below the connection of the separated or divided branch 24a to said rectilinear branch. The presence of the restriction 106 permits a preferred outflow of the rinsing water to the branch 24a, which is immersed in the cup 10 located at the working station, when the corresponding ramp 86 is in the bottom position.

As a result of this arrangement, a brief opening of the electrovalve placed in the tube 24 makes it possible to empty the cup 10 by starting the syphon formed between the branches 24a and 24b. The rinsing of the cup 10 can then be brought about by opening the electrovalve for a longer time, in order to eject rinsing liquid using the branch 24a.

Although the working station can be a fixed station located within the enclosure 12, the installation advantageously has means making it possible to move several cups 10 to said station, so that the uranium dosing process can be performed in automated manner and successively on each of the solutions contained in the cups.

Figure 5:
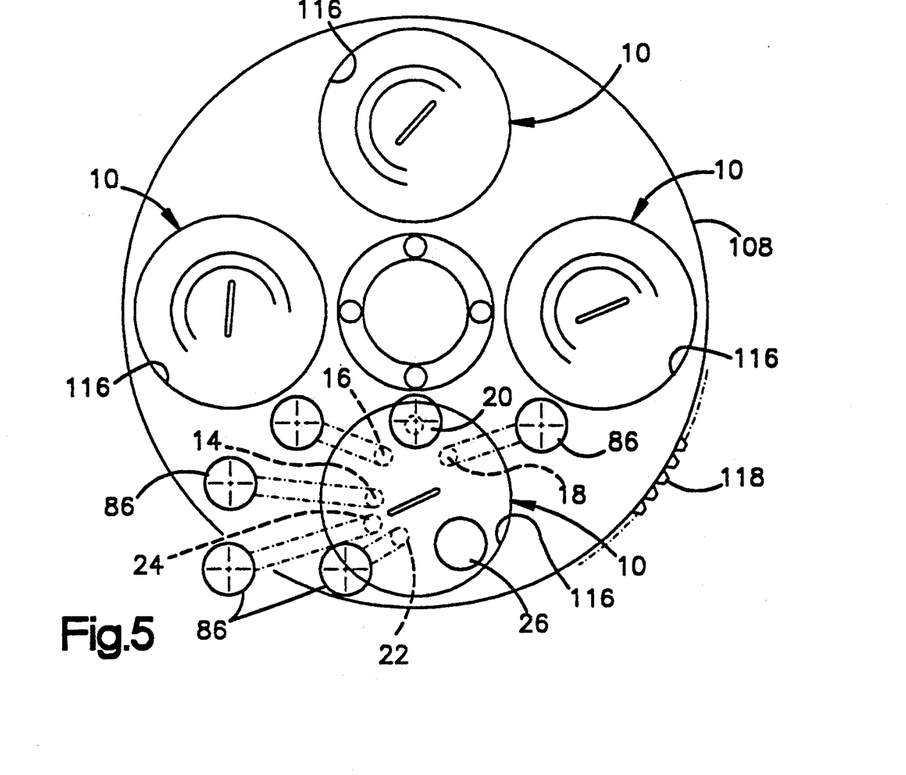
FIG. 5 A sectional view along line V—V of FIG. 3.

In the embodiment more particularly illustrated in FIGS. 1, 3 and 5, the movement of the cups is brought about by a rotary horizontal table 108. As is very diagrammatically illustrated in FIG. 2, said table 108 is supported by a horizontal arm 110 formed at the lower end of a vertical beam 112 fixed e.g. by means of not shown screws to the support plate 78 (FIG. 3). More specifically, the horizontal arm 110 carries a vertical spindle 114 on its upper face and the table 108 is mounted on said spindle 114 so that it can freely rotate.

As is more particularly illustrated in FIGS. 3 and 4, on its upper face the table 108 has four cavities 116 with a circular horizontal section constituting receptacles for four cups 10. The cavities 116 are regularly distributed around the rotation axis of the table 108 at 90 from one another.

To permit the movement of each of the cups 10 located in the cavities 116 to the working station positioned approximately vertically below the solid body 80, the table 108 is provided on its periphery with a toothed ring 118 on which is engaged a pinion 120 supported by a vertical driving shaft 122, in accordance with the arrangement shown in FIG. 3. The upper part of the driving shaft 122 tightly traverses the support plate 78, so as to be driven by a geared motor means 124, which has a direct current motor controlled by the central control computer, when a dosing cycle followed by draining and rinsing operations with respect to the cup is brought to an end.

The output shaft 122 of the means 124 also drives, above the plate 78, a pinion 126 which is engaged on a gear 128 rotating a reference mark 130. For each rotation, said reference mark 130 passes in front of an optoelectronic sensor 132 mounted on the plate 78.

The reduction ratios existing on the one hand between the pinion 120 and the toothed ring 118 and on the other between the pinion 126 and the gear 128 are chosen in such a way that a rotation by one turn of the mark 130 corresponds to a rotation of a quarter turn of the table 108. Thus, whenever the mark 130 passes in front of the sensor 132, the table 108 has rotated by a quarter turn.

The presence information of the reference mark 130 in front of the optoelectronic sensor 132 is transmitted to the central control computer 40, which automatically stops the geared motor means 124. A new cup 10 is then located at the working station below the solid body 80 and a new dosing cycle can be initiated.

FIGS. 2 and 3 show the electromagnetic stirrer 28 mounted on the horizontal arm 110, so that its vertical axis is aligned with the axis of the cup 10 at the working station.

As is shown in greater detail in FIG. 3, the cups 10 advantageously have in their bottom a circular recess 134, which is formed, along the cup axis, by a downward displacement of the central planar part of the bottom with respect to its planar peripheral part.

In order to stir the solution contained in the cup 10, a magnetic bar 136 is placed in the circular recess 134. Advantageously and as shown in the left-hand part of FIG. 3, said magnetic bar 136 has a triangular section. Obviously, the magnetic bars 136 are put into place by an operator in each of the cups 10, before the latter arrive in front of the working station under the action of the rotation of the table 108.

The preceding description concerning an installation more particularly intended for dosing uranium in the presence of plutonium and fission products, in the aqueous or organic phase, according to the Davies and Gray method, reveals the various advantages resulting from this installation, particularly as regards to the arrangements making it possible to avoid an inopportune dropping of reagents into the cup containing the solution being dosed and with regards to the draining and rinsing of the cup when dosing is at an end.

It is clear that these advantages are retained no matter what chemical reactions are performed in the working station and no matter what reactants are involved. From this standpoint, it should be noted that the installation according to the invention makes it possible to carry out any sequence of chemical reactions in a cup, independently of whether the latter is initially empty or not. Moreover, in a simplified version of such an installation, the putting into place of the cups or corresponding containers at the working station can be performed manually by the operator or by the different rotary table transfer means described, such as a stepwise conveyor. Moreover it is clear that when the chemical reactions performed relate to reactants not requiring special protection, the inventive installation can be used outside any confinement enclosure. Finally, it should be noted that the means described make it possible to rotate the ramps supporting the reagent distribution tubes when the latter rise into their inactive position can be replaced by any technically equivalent means, such as a system of rails or cams.

We claim:

1. Apparatus for performing several successive chemical reactions within a single container, comprising:
   a working station adapted to receive the container,
   at least two chemical reactant arrival tubes, each tube having a first end issuing above the working station and an opposite, second end immersed in a distribution drum containing a chemical reactant,
   control means for moving the first end of each tube between an upper, inactive position and a lower, reactant injection position, cam means for displacing the first end of at least one of said tubes in a lateral direction with respect to said container upon actuation of said control means such that the first end is placed in the container when the said at least one tube is in the lower, reactant injection position, and is laterally displaced by the cam means with respect to the container upon movement of the said at least one tube toward the upper, inactive position by the control means.

2. Apparatus according to claim 1, wherein the said at least one tube has a vertically axed, straight portion, able to slide and rotate in a support, the first end of said at elast one tube being displaced with respect to said vertical axis, and said cam means incorporate means for pivoting the said at least one tube about said vertical axis.

3. Apparatus according to claim 2, wherein the means for pivoting the said at least one tube incorporate a pawl integral with the said straight portion of the latter and which is received in an inwardly curved slot formed in the support.

4. Apparatus according to claim 1, wherein moving means are provided for presenting in turn several containers to a working station above which are located the first ends of said tubes.

5. Apparatus according to claim 4, wherein the moving means comprise a horizontal table equipped with cavities for receiving the containers, which are regularly distributed about a vertical axis, as well as driving means for sequentially rotating the table about said axis, when said successive chemical reactions have been finished for a particular container.

6. Apparatus according to claim 1, wherein an electromagnetic stirrer is positioned beneath the container and a magnetic bar is placed in a circular recess formed in the bottom of the container.

7. Apparatus according to claim 6, wherein the magnetic bar has a triangular cross-section.

8. Apparatus according to claim 1, further comprising a vertically oriented electrode which is bundled with said at least one tube and on which acts said control means.

9. Apparatus according to claim 1, wherein said at least one tube comprises a container draining and rinsing liquid supply tube, the first end of said draining and rinsing liquid supply tube having an h-shaped ramp, whereof a short, divided branch enters the container and whereof a short, rectilinear branch outside the container has a narrowing below the connection of the short branch.

10. Apparatus 1 according to claim 1, wherein said tubes comprise a diluting water supply tube having a T-shaped distributing ramp at its first end.

11. Apparatus according to claim 1 also comprising a control station making it possible to perform in an automated manner said successive chemical reactions, controlling the control means and the means for distributing the reactants within tubes.

12. Apparatus according to claim 1, wherein the container is placed in a tight confinement enclosure, whereof an upper wall is provided with a plate tightly traversed by said reactant arrival tubes, said plate supporting a container-carrying beam within the enclosure, together with control means outside the enclosure.

* * * * *

UNITED STATES PATENT AND TRADEMARK OFFICE
CERTIFICATE OF CORRECTION

PATENT NO. : 5,328,662
DATED : July 12, 1994
INVENTOR(S) : Ringot et al.

It is certified that error appears in the above-identified patent and that said Letters Patent is hereby corrected as shown below:

On the title page, item [75] inventors, second inventor's city should read --Tourlaville--.

Column 9, line 14, (Claim 2, line 4), delete "elast" and insert --least--.

Column 10, line 19, (Claim 10, line 1), delete "1" (first occurrence).

Column 10, line 25, (Claim 11, line 4), delete "the" (second occurrence).

Column 10, line 26, (Claim 11, line 5), after "within" insert --the--.

Signed and Sealed this

Twenty-fourth Day of January, 1995

*Attest:*

*Attesting Officer*

BRUCE LEHMAN

*Commissioner of Patents and Trademarks*